(12) United States Patent
Inaba et al.

(10) Patent No.: US 6,432,896 B1
(45) Date of Patent: Aug. 13, 2002

(54) DETERGENT COMPOSITION COMPRISING AN AMPHOTERIC SURFACTANT SYSTEM

(75) Inventors: Sayaka Inaba; Hideyuki Hanazawa, both of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/581,502

(22) PCT Filed: Dec. 7, 1998

(86) PCT No.: PCT/JP98/05521

§ 371 (c)(1),
(2), (4) Date: Jun. 16, 2000

(87) PCT Pub. No.: WO99/31208

PCT Pub. Date: Jun. 24, 1999

(30) Foreign Application Priority Data

Dec. 18, 1997 (JP) .............................. 9-349121

(51) Int. Cl.⁷ ............................... C11D 1/90
(52) U.S. Cl. ................. 510/123; 510/119; 510/126; 510/130; 510/405; 510/433; 510/477; 510/480; 510/490; 510/501
(58) Field of Search ............... 510/119, 130, 510/123, 126, 405, 433, 477, 480, 490, 501

(56) References Cited

U.S. PATENT DOCUMENTS

| | | | | |
|---|---|---|---|---|
| 4,122,043 A | * | 10/1978 | Kersnar et al. | 252/527 |
| 4,207,215 A | | 6/1980 | Bolan | 252/542 |
| 4,835,149 A | * | 5/1989 | Burke et al. | 514/188 |
| 4,847,004 A | * | 7/1989 | McLeod | 252/527 |
| 4,876,034 A | | 10/1989 | Hirota et al. | |
| 4,946,136 A | | 8/1990 | Fishlock-Lomax | 252/546 |
| 5,156,773 A | * | 10/1992 | Kochavi et al. | 252/547 |
| 5,811,086 A | * | 9/1998 | Matsuzawa et al. | 424/70.13 |
| 5,854,199 A | * | 12/1998 | Oshimura et al. | 510/501 |

FOREIGN PATENT DOCUMENTS

| | | |
|---|---|---|
| EP | 269939 | 7/1988 |
| EP | 0 834 307 A3 | 4/1998 |
| EP | 0 976 392 A1 | 2/2000 |
| JP | 63-161080 | 7/1988 |
| WO | 94/18292 | 8/1994 |
| WO | 96/17590 | 6/1996 |

* cited by examiner

*Primary Examiner*—Charles Boyer
(74) *Attorney, Agent, or Firm*—Oblon, Spivak, McClelland, Maier & Neustadt, P.C.

(57) ABSTRACT

A detergent composition contains the following components (a) and (b):

(a) an amphoteric surfactant 2 to 35 wt. %, (b) a compound which is other than the component (a) and contains, in its molecule, a carboxyl group and an amino group or a quaternary ammonium group 6 to 40 wt. %. This composition is easily thickened without using a thickener, and has excellent temperature stability and washing with it imparts the skin with good touch feeling.

13 Claims, No Drawings

DETERGENT COMPOSITION COMPRISING AN AMPHOTERIC SURFACTANT SYSTEM

TECHNICAL FIELD

The present invention relates to a detergent composition which is thickened without using a thickener, has excellent temperature stability and can impart the skin with good touch feeling after washing.

BACKGROUND ART

It is the common practice to gel a detergent composition for the skin or hair by using a thickener in order to prevent it from easily flowing away from the body upon use. Incorporation of a thickener in a detergent composition is however accompanied with the problem that stirring under heat is necessary and thus, the treatment of it is very cumbersome. Moreover, a gel thus obtained involves a problem in stability, because it is easily influenced by a temperature or pH.

With a view to overcoming these problems, a viscous composition (Japanese Patent Application Laid-Open No. SHO 58-79099) which is gelled by the addition of amidobetaine and salts without using an ordinary thickener is proposed. Such a composition, when used as a detergent composition, cannot impart the skin with moisturized feeling after washing and good skin touch is not available.

An object of the present invention is therefore to provide a detergent composition which can be thickened easily without using a thickener, has excellent temperature stability and can impart the skin with good touch feeling after washing.

DISCLOSURE OF THE INVENTION

The present inventors combined an amphoteric surfactant and a compound containing, in the molecule thereof, a carboxyl group and an amino group or a quaternary ammonium group at a specific ratio. It has been found that based on this combination, a detergent composition which is thickened easily by mixing these components at room temperature without using a thickener, has excellent temperature stability and after washing with it, can impart the skin with good touch feeling such as moisturized feeling is available. Thus, the present inventors completed the present invention.

In the present invention, there is thus provided a detergent composition comprising the following components (a) and (b):

(a) an amphoteric surfactant 2 to 35 wt. %, and (b) a compound which is other than the component (a) and contains, in its molecule, a carboxyl group and an amino group or a quaternary ammonium group 6 to 40 wt. %.

BEST MODE FOR CARRYING OUT THE INVENTION

As the amphoteric surfactant (a) to be used in the present invention, carboxybetaine amphoteric surfactants are preferred. Specific examples include alkylamidobetaines (alkyl-$CONH(CH_2)_n$—$N^+(CH_3)_2$—$CH_2COO^-$), alkylaminobetaines (alkyl-$NH(CH_2)_n$—$N^+(CH_3)_2$—$CH_2COO^-$), alkylbetaines (alkyl-$N^+(CH_3)_2$—$CH_2COO^-$), and 2-alkyl-N-carboxymethyl-N-hydroxyethylimidazoliniumbetaines. Among them, those having a $C_{8-20}$ alkyl group or acyl group are particularly preferred.

As the component (a), one or more amphoteric surfactants can be used in combination. The component (a) is incorporated in a total amount of 2 to 35 wt. % (which will hereinafter be called %, simply), preferably 2 to 20% based on the whole composition. Amounts less than 2% cannot thicken the system sufficiently, while those exceeding 35% may solidify the system and damage the appearance.

The compound (b) used in the present invention is other than the component (a) and contains, in its molecule, a carboxyl group and an amino group or a quaternary ammonium group. As such compounds, neutral amino acids, betaine compounds and ethylenediaminetetraacetate salts are preferred. Specific examples of the neutral amino acid include glycine, sarcosine, L-serine, β-alanine and aminobutyric acid. Specific examples of the betaine compounds include those having 1 to 5 carbon atoms in each of the alkyl chains, for example, trimethylglycine, trimethylserine, hydroxyethyldimethylglycine and monoethanolcarboxybetaine ($HOCH_2CH_2N^+$—$(CH_3)_2$—$CH_2CH_2CH_2COO^-$).

Among them, betaine compounds having 1 to 5 carbon atoms in each of the alkyl chains are preferred, with trimethylglycine being more preferred, because it brings about sufficient thickening effects and moisture retention effects.

As the component (b), one or more of the above-described compounds can be used in combination. The component (b) is added in an amount of 6 to 40%, preferably 6 to 30%, particularly preferably 6 to 20% based on the whole composition. Amounts less than 6% cannot thicken the system sufficiently, while those exceeding 40% happen to solidify the system. For the use as a detergent, amounts up to 40% are preferred.

It is preferred that the weight ratio of the component (a) to the component (b) ((a)/(b)) falls within a range of 1/10 to 10/1, particularly from 1/5 to 5/1 and more preferably from 1/5 to 3/1. At a weight ratio within the above-described range, thickening occurs easily and a gel composition is available.

To the detergent composition of the present invention, a surfactant other than the above-described one can also be added. Examples include anionic surfactants: such as alkyl sulfate salts, alkyl sulfonate salts, alkyl phosphate salts, polyoxyethylene alkyl sulfate salts, alkylbenzene sulfonate salts, N-acylsarcosine salts, N-acyl-N-methyltaurine salts, alfaolefin sulfonate salts, higher fatty acid ester sulfonate salts, alkyl ether acetate salts, polyoxyethylene alkyl ether acetate salts and fatty acid soap; and nonionic surfactants such as fatty acid amides, polyoxyethylene alkyl ethers, saccharide esters, saccharide ethers and saccharide amides.

In addition, humectants such as propylene glycol, sorbitol and glycerin, pearling agents, perfumes, colorants, ultraviolet absorbers, antioxidants, bactericides, anti-inflammatory agents and antiseptics can be added as another additive.

The detergent composition of the present invention can be obtained as a transparent gel composition by mixing the components (a) and (b), optional components and water at room temperature, thereby easily thickening. It can also be prepared as an opaque composition by adding a turbidity imparting agent. Water is added in an amount of 40 to 70% based on the whole composition, with 50 to 70% being particularly preferred. By adjusting the amount of each of the components, the desired viscosity is available. For example, viscosity at 25° C. is preferably adjusted to 1,000 to 1,000,000 mPa.s, with 10,000 to 100,000 mPa.s being particularly preferred.

The detergent composition of the present invention thus available is used for washing of the skin, hair or the like and it is particularly suited for use as a skin detergent, more preferably face wash.

EXAMPLES

Example 1

Detergent compositions each having the components as shown in Table 1 were prepared and their manufacturing ease, form, temperature stability and touch feeling of the skin after washing were evaluated. The results are shown in Table 1.

Evaluation Method (1) Manufacturing Ease

A: can be prepared easily by stirring at room temperature without heating

C: cannot be prepared easily, because stirring under heat is necessary (2) Form

The form just after preparation was visually observed.

(3) Temperature Stability

The appearance after storage for 1 day at −5° C. was visually observed.

A: same as that just after preparation and is transparent.

B: slightly turbid

C: turbid (4) Touch Feeling of the Skin after Washing

The touch feeling of the skin after washing with a detergent composition was evaluated by a panel of 10 Japanese female experts in their twenties to thirties in accordance with the below-described ranking standards and a mean score was calculated. The score of 4 or greater is indicated as A, that of 2.5 or greater but less than 4 is indicated as B and that less than 2.5 is indicated as C.

5: excellent moisturized and smooth touch feeling

4: good moisturized and smooth touch feeling

3: average moisturized and smooth touch feeling

2: not so good in moisturized and smooth touch feeling.

1: neither moisturized touch feeling nor smooth touch feeling is imparted.

TABLE 1

| Component | Invention product | | Comparative product | |
|---|---|---|---|---|
| (%) | 1 | 2 | 1 | 2 |
| 30% Lauroylamidopropylbetaine solution (product of Kao Corp.) | 60 | 60 | 60 | 5 |
| Sodium sulfate (product of Katayama Chemical) | | | 20 | |
| Trimethlyglycine (product of Asahi Kasei Foods | 20 | | | 5 |
| Hydroxyethyldimethylglycine (product of Kao Corp.) | 2 | 20 | | |
| Purified water | 20 | 20 | 20 | 90 |
| Manufacturing ease | A | A | C | A |
| Form | Transparent gel | Transparent gel | Transparent gel | Transparent (not thickened) |
| Temperature stability | A | A | C | A |
| Touch feeling of washed skin | A | A | C | B |

Example 2

A detergent composition composed of the below-described components was prepared in a manner known per se in the art.

| (Component) | (%) |
|---|---|
| 30% Lauroylamidopropylbetaine solution | 15 |
| 25% Polyoxyethylene (2.0) sodium lauryl sulfate | 5 |
| Trimethylglycine | 15 |
| 70% Sorbitol | 10 |
| 50% Citric acid | 0.1 |
| Perfume, antiseptic | q.s. |
| Purified water | balance |

Example 3

A detergent composition composed of the below-described components was prepared in a manner known per se in the art.

| (Component) | (%) |
|---|---|
| 30% Laurylbetaine solution | 20 |
| 50% Potassium laurylphosphate | 20 |
| Serine | 15 |
| 86% Glycerin | 3 |
| Perfume, antiseptic | q.s. |
| Purified water | Balance |

Each of the detergent compositions obtained in Examples 2 and 3 was thickened easily, assumed a transparent appearance and had excellent temperature stability. Further, the skin washed with it had favorable touch feeling.

INDUSTRIAL APPLICABILITY

The detergent composition according to the present invention is easily thickened by mixing its components at room temperature even without using a thickener and has excellent temperature stability, and imparts moisturized feeling to the washed skin. Thus the skin after washing has good touch feeling.

What is claimed is:

1. A detergent composition comprising the following components (a) and (b):
   (a) carboxy betaine surfactant in an amount of 2 to 35% by weight of the composition; wherein said carboxy betaine surfactant comprises $C_{8-20}$ alkyl or $C_{8-20}$ acyl groups: and
   (b) betaine compounds which comprise five carbon atoms or less in each of the alkyl chains of its molecule in an amount of 6 to 40% by weight of the composition.

2. The detergent composition of claim 1, wherein said carboxy betaine surfactant in (a) is selected from the group consisting of alkylamidobetaines, alkylaminobetaines, alkylbetaines, and 2-alkyl-N-carboxymethyl-N-hydroxyethylimidazoliniumbetaines.

3. The detergent composition of claim 1, wherein said carboxy betaine surfactant in (a) is in an amount of 2 to 20% by weight of the composition.

4. The detergent composition of claim 1, wherein said betaine compound in (b) is in an amount of 6 to 30% by weight of the composition.

5. The detergent composition of claim 1, wherein said betaine compound (b) is in an amount of 6 to 20% by weight of the composition.

6. The detergent composition of claim 1, further comprising at least one of neutral amino acids and ethylenediaminetetraacetate.

7. The detergent composition of claim 1, wherein said betaine compound in (b) is selected from the group consisting of trimethylglycine, trimethylserine, hydroxyethyldimethylglycine, and monoethanolcarboxybetaine.

8. The detergent composition of claim 1, wherein the weight ratio of (a) to (b) is from 1:10 to 10:1.

9. The detergent composition of claim 1, wherein the weight ratio of (a) to (b) is from 1:5 to 5:1.

10. The detergent composition of claim 1, wherein the weight ratio of (a) to (b) is from 1:5 to 3:1.

11. The detergent composition of claim 1, further comprising at least one humectant selected from the group consisting of propylene glycol, sorbitol, and glycerin.

12. The detergent composition of claim 1, further comprising at least one anionic surfactant selected from the group consisting of alkyl sulfate salts, alkyl sulfonate salts, alkyl phosphate salts, polyoxyethylene alkyl sulfate salts, alkylbenzene sulfonate salts, N-acylsarcosine salts, N-acyl-N-methyltaurine salts, alfaolefin sulfonate salts, higher fatty acid ester sulfonate salts, alkyl ether acetate salts, polyoxyethylene alkyl ether acetate salts, and fatty acid soap.

13. The detergent composition of claim 1, further comprising at least one nonionic surfactant selected from the group consisting of fatty acid amides, polyoxyethylene alkyl ethers, saccharide esters, saccharide ethers and saccharide amides.

* * * * *